United States Patent
Dalebout et al.

(10) Patent No.: US 11,534,655 B2
(45) Date of Patent: Dec. 27, 2022

(54) STRENGTH EXERCISE MECHANISMS

(71) Applicant: iFIT Inc., Logan, UT (US)

(72) Inventors: William T. Dalebout, North Logan, UT (US); Gordon Cutler, Providence, UT (US)

(73) Assignee: iFIT Inc., Logan, UT (US)

( * ) Notice: Subject to any disclaimer, the term of this patent is extended or adjusted under 35 U.S.C. 154(b) by 61 days.

(21) Appl. No.: 17/159,814

(22) Filed: Jan. 27, 2021

(65) Prior Publication Data

US 2021/0146191 A1    May 20, 2021

Related U.S. Application Data

(63) Continuation of application No. 15/245,473, filed on Aug. 24, 2016, now Pat. No. 10,940,360.

(Continued)

(51) Int. Cl.
*A63B 22/02* (2006.01)
*A63B 21/00* (2006.01)
(Continued)

(52) U.S. Cl.
CPC ............ *A63B 22/02* (2013.01); *A61B 5/6895* (2013.01); *A63B 21/00047* (2013.01); *A63B 21/4035* (2015.10); *A63B 22/0007* (2013.01); *A63B 22/0046* (2013.01); *A63B 22/0235* (2013.01); *A63B 23/03516* (2013.01); *A63B 71/0622* (2013.01); *G09B 19/0038* (2013.01); *G16H 20/30* (2018.01); *A61B 5/0205* (2013.01); *A61B 5/1128* (2013.01); *A61B 2503/10* (2013.01); *A63B 1/00* (2013.01); *A63B 17/04* (2013.01); *A63B 21/068* (2013.01); *A63B 21/0726* (2013.01); *A63B 21/16* (2013.01); *A63B 21/169* (2015.10); *A63B 21/1618* (2013.01); *A63B 22/0023* (2013.01); *A63B 23/0216* (2013.01); *A63B 23/03525* (2013.01); *A63B 23/03541* (2013.01); *A63B 23/03558* (2013.01); *A63B 23/1218* (2013.01); *A63B 23/1227* (2013.01); *A63B 23/1236* (2013.01);
(Continued)

(58) Field of Classification Search
None
See application file for complete search history.

(56) References Cited

U.S. PATENT DOCUMENTS 4,625,962 A * 12/1986 Street ................. A63B 69/06
                                                                482/54
8,075,453 B1 * 12/2011 Wilkinson .......... A63B 21/4019
                                                                 482/8
(Continued)

FOREIGN PATENT DOCUMENTS

WO    WO-2009014330 A1 *  1/2009 ............. A63B 21/04

*Primary Examiner* — Sundhara M Ganesan
*Assistant Examiner* — Shila Jalalzadeh Abyaneh
(74) *Attorney, Agent, or Firm* — Ray Quinney & Nebeker P.C.; Paul N. Taylor

(57) ABSTRACT

A treadmill includes a frame, an exercise deck attached to the frame, and a first handle movably attached to the frame. The first handle has a first orientation where the first handle is positioned within a region above the exercise deck and stabilized to support a user's weight during a body weight exercise, and a second orientation where the first handle is positioned away from the region above the exercise deck.

20 Claims, 10 Drawing Sheets

Related U.S. Application Data

(60) Provisional application No. 62/210,318, filed on Aug. 26, 2015.

(51) Int. Cl.

| | | |
|---|---|---|
| *A63B 23/035* | (2006.01) | |
| *A63B 22/00* | (2006.01) | |
| *A63B 71/06* | (2006.01) | |
| *A63B 21/068* | (2006.01) | |
| *A63B 23/12* | (2006.01) | |
| *A63B 23/02* | (2006.01) | |
| *A63B 23/00* | (2006.01) | |
| *G16H 20/30* | (2018.01) | |
| *A61B 5/00* | (2006.01) | |
| *G09B 19/00* | (2006.01) | |
| *A63B 1/00* | (2006.01) | |
| *A63B 17/04* | (2006.01) | |
| *A63B 21/16* | (2006.01) | |
| *A63B 24/00* | (2006.01) | |
| *A61B 5/11* | (2006.01) | |
| *A61B 5/0205* | (2006.01) | |
| *A63B 21/072* | (2006.01) | |

(52) U.S. Cl.
CPC ..... *A63B 24/0087* (2013.01); *A63B 2023/006* (2013.01); *A63B 2071/063* (2013.01); *A63B 2071/065* (2013.01); *A63B 2071/0638* (2013.01); *A63B 2071/0655* (2013.01); *A63B 2071/0658* (2013.01); *A63B 2220/05* (2013.01); *A63B 2220/10* (2013.01); *A63B 2220/13* (2013.01); *A63B 2220/17* (2013.01); *A63B 2220/20* (2013.01); *A63B 2220/30* (2013.01); *A63B 2220/31* (2013.01); *A63B 2220/52* (2013.01); *A63B 2220/62* (2013.01); *A63B 2220/70* (2013.01); *A63B 2220/72* (2013.01); *A63B 2220/73* (2013.01); *A63B 2220/74* (2013.01); *A63B 2220/75* (2013.01); *A63B 2220/806* (2013.01); *A63B 2220/807* (2013.01); *A63B 2225/20* (2013.01); *A63B 2225/50* (2013.01); *A63B 2230/00* (2013.01); *A63B 2230/01* (2013.01); *A63B 2230/06* (2013.01); *A63B 2230/207* (2013.01); *A63B 2230/30* (2013.01); *A63B 2230/40* (2013.01); *A63B 2230/62* (2013.01); *A63B 2230/75* (2013.01)

(56) References Cited

U.S. PATENT DOCUMENTS

| | | | |
|---|---|---|---|
| 9,186,552 B1* | 11/2015 | Deal | A63B 71/0619 |
| 2005/0277520 A1* | 12/2005 | Van Waes | A63B 71/04 |
| | | | 482/54 |
| 2006/0035755 A1* | 2/2006 | Dalebout | A63B 24/00 |
| | | | 482/52 |
| 2006/0035768 A1* | 2/2006 | Kowallis | A63B 21/00072 |
| | | | 482/121 |
| 2006/0135322 A1* | 6/2006 | Rocker | A63B 21/072 |
| | | | 482/8 |
| 2010/0317488 A1* | 12/2010 | Cartaya | A63B 71/0622 |
| | | | 482/5 |
| 2015/0352396 A1* | 12/2015 | Dalebout | A63B 22/02 |
| | | | 482/54 |
| 2016/0023043 A1* | 1/2016 | Grundy | A61B 5/681 |
| | | | 482/8 |

\* cited by examiner

STRENGTH EXERCISE MECHANISMS

CROSS-REFERENCE TO RELATED APPLICATIONS

This application is a continuation of U.S. patent application Ser. No. 15/245,473 filed Aug. 24, 2016, which claims priority to U.S. Provisional Patent Application No. 62/210,318 filed on Aug. 26, 2015, which applications are herein incorporated by reference for all that they disclose.

BACKGROUND

Aerobic exercise is a popular form of exercise that improves one's cardiovascular health by reducing blood pressure and providing other benefits to the human body. Aerobic exercise generally involves low intensity physical exertion over a long duration of time. Typically, the human body can adequately supply enough oxygen to meet the body's demands at the intensity levels involved with aerobic exercise. Popular forms of aerobic exercise include running, jogging, swimming, and cycling among other activities. In contrast, anaerobic exercise typically involves high intensity exercises over a short duration of time. Popular forms of anaerobic exercise include strength training and short distance running.

Many choose to perform aerobic exercises indoors, such as in a gym or their home. Often, a user uses an aerobic exercise machine to have an aerobic workout indoors. One such type of aerobic exercise machine is a treadmill, which is a machine that has a running deck attached to a support frame. The running deck can support the weight of a person using the machine. The running deck incorporates a tread belt that is driven by a motor. A user can run or walk-in place on the tread belt by running or walking at the tread belt's speed. The speed and other operations of the treadmill are generally controlled through a control module that is also attached to the support frame and within a convenient reach of the user. The control module can include a display, buttons for increasing or decreasing a speed of the conveyor belt, controls for adjusting a tilt angle of the running deck, or other controls. Other popular exercise machines that allow a user to perform aerobic exercises indoors include elliptical machines, rowing machines, stepper machines, and stationary bikes to name a few.

One type of dual use exercise machine is disclosed in U.S. Pat. No. 5,000,440 issued to Robert P. Lynch. In this reference, an exercise apparatus combines a treadmill with an upper body muscle stressing device that allows for simultaneous upper body exercise with aerobic exercise. This reference is incorporated by reference for all that it discloses.

SUMMARY

In one embodiment of the present invention, a treadmill includes a frame, an exercise deck attached to the frame, and a first handle movably attached to the frame. The first handle has a first orientation where the first handle is positioned within a region above the exercise deck and stabilized to support a user's weight during a body weight exercise, and a second orientation where the first handle is positioned away from the region above the exercise deck.

The first handle may be aligned with a length of the exercise deck in the first orientation and the first handle is transverse to the length of the exercise deck when in the second orientation.

The first handle may be pivotally attached to the frame.

A second handle may be movably attached to the frame is spaced an adjustable distance away from the first handle.

At least one of the first handle or the second handle may move laterally with respect to the frame.

The first handle and the second handle may be spaced approximately a human body width apart in the first orientation.

The treadmill further may include a repetition sensor to count the number of times that a user performs the body weight exercise.

The treadmill further may include a weight sensor to generate a weight value of a user applying their body weight to the first handle and the second handle.

The treadmill may include a display to present a repetition count of the body weight exercise.

The treadmill may include a display to present a body weight exercise calorie burn value based on a performance of the body weight exercise.

The treadmill may include a processor and memory.

The memory may include programmed instructions to cause the processor to calculate an exercise deck calorie burn value based on a performance of an exercise with the exercise deck.

The memory may include programmed instructions to cause the processor to calculate a body weight calorie burn value based on a performance of the body weight exercise.

The memory may include programmed instructions to cause the processor to add the exercise deck calorie burn value to the body weight exercise calorie burn value to generate a workout calorie burn value.

The memory may include programmed instructions to cause the processor to present the workout calorie burn value in a display.

The body weight exercise may be a dipping exercise.

The treadmill may include a tread belt incorporated into the exercise deck wherein the first handle is moved into the second orientation during a performance of an exercise on the tread belt.

The treadmill may include a push-up bar attached to the frame.

The treadmill may include a push-up bar attached to the exercise deck.

In one embodiment, a treadmill includes a frame, an exercise deck attached to the frame, a first handle movably attached to the frame, and a second handle movably attached to the frame and spaced a first distance from the first handle. The first handle and the second handle each comprise a first orientation where the first handle and the second handle are positioned within a region above the exercise deck and stabilized to support a user's weight during a body weight exercise and a second orientation where the first handle and the second handle are positioned away from the region above the exercise deck. The first handle and the second handle are spaced a human body width apart in the first orientation and capable of supporting a user's weight during a body weight exercise. The treadmill further includes a repetition sensor to count the number of times that a user performs the body weight exercise.

The first handle and the second handle may be spaced a human body width apart in the first orientation and capable of supporting a user's weight during a body weight exercise.

The treadmill may include a repetition sensor to count the number of times that a user performs the body weight exercise.

The first handle and the second handle may be aligned with a length of the exercise deck in the first orientation, and the first handle and the second handle are transverse to the length of the exercise deck in the second orientation.

At least one of the first handle and the second handle may be slidably attached to the frame.

The treadmill may further include a display to present a repetition count of the body weight exercise based on information gathered from the repetition sensor.

In one embodiment of the invention, a treadmill includes a frame, an exercise deck attached to the frame, a first handle movably attached to the frame, a second handle movably attached to the frame and spaced a first distance from the first handle. The first handle and the second handle each comprise a first orientation where the first handle and the second handle are positioned within a region above the exercise deck and stabilized to support a user's weight during a body weight exercise and a second orientation where the first handle and the second handle are positioned away from the region above the exercise deck. The first handle and the second handle are aligned with a length of the exercise deck in the first orientation, and the first handle and the second handle are transverse to the length of the exercise deck in the second orientation. The first handle and the second handle are spaced a human body width apart in the first orientation and capable of supporting a user's weight during a body weight exercise. The treadmill also includes a repetition sensor to count the number of times that a user performs the body weight exercise, and a display to present a repetition count of the body weight exercise based on information gathered from the repetition sensor. The treadmill also includes a processor and memory, the memory comprising programmed instructions to cause the processor to calculate an exercise deck calorie burn value based on an exercise deck exercise, calculate a body weight calorie burn value based on the body weight exercise, add the exercise deck calorie burn value to the body weight exercise calorie burn value to generate a workout calorie burn value, and present the workout calorie burn value in the display.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

For purposes of this disclosure, the term "aligned" means parallel, substantially parallel, or forming an angle of less than 35.0 degrees. For purposes of this disclosure, the term "transverse" means perpendicular, substantially perpendicular, or forming an angle between 55.0 and 125.0 degrees. Also, for purposes of this disclosure, the term "length" means the longest dimension of an object. Also, for purposes of this disclosure, the term "width" means the dimension of an object from side to side. For the purposes of this disclosure, the term "above" generally means superjacent, substantially superjacent, or higher than another object although not directly overlying the object.

Figure 1A:
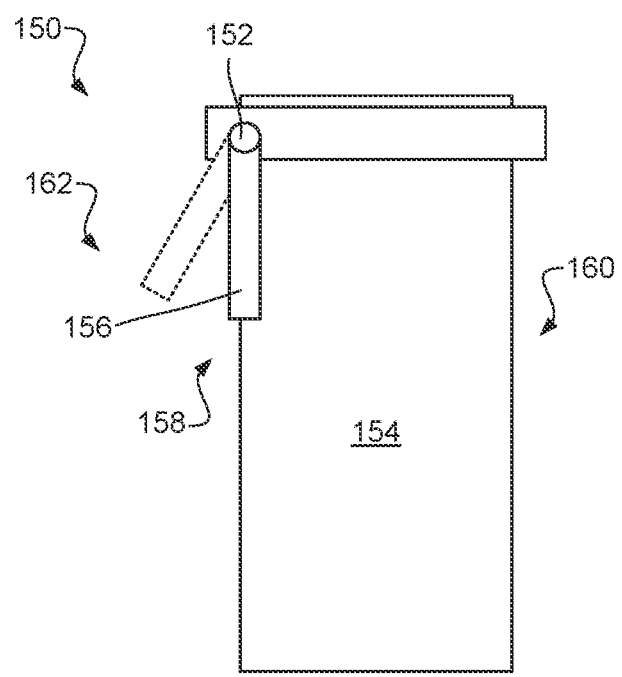
FIG. 1a illustrates a top view of an example of treadmill in accordance with the present disclosure.

Particularly, with reference to the figures, FIG. 1a illustrates an example of a treadmill 150 in accordance with the present disclosure. The treadmill 150 includes a frame 152, an exercise deck 154 attached to the frame 152, and a first handle 156 movably attached to the frame 152. The first handle 156 has a first orientation 158 where the first handle 156 is positioned within a region 160 above the exercise deck 154 and stabilized to support a user's weight during a body weight exercise, and a second orientation 162 where the first handle 156 is positioned away from the region 160 above the exercise deck 154.

Figure 1B:
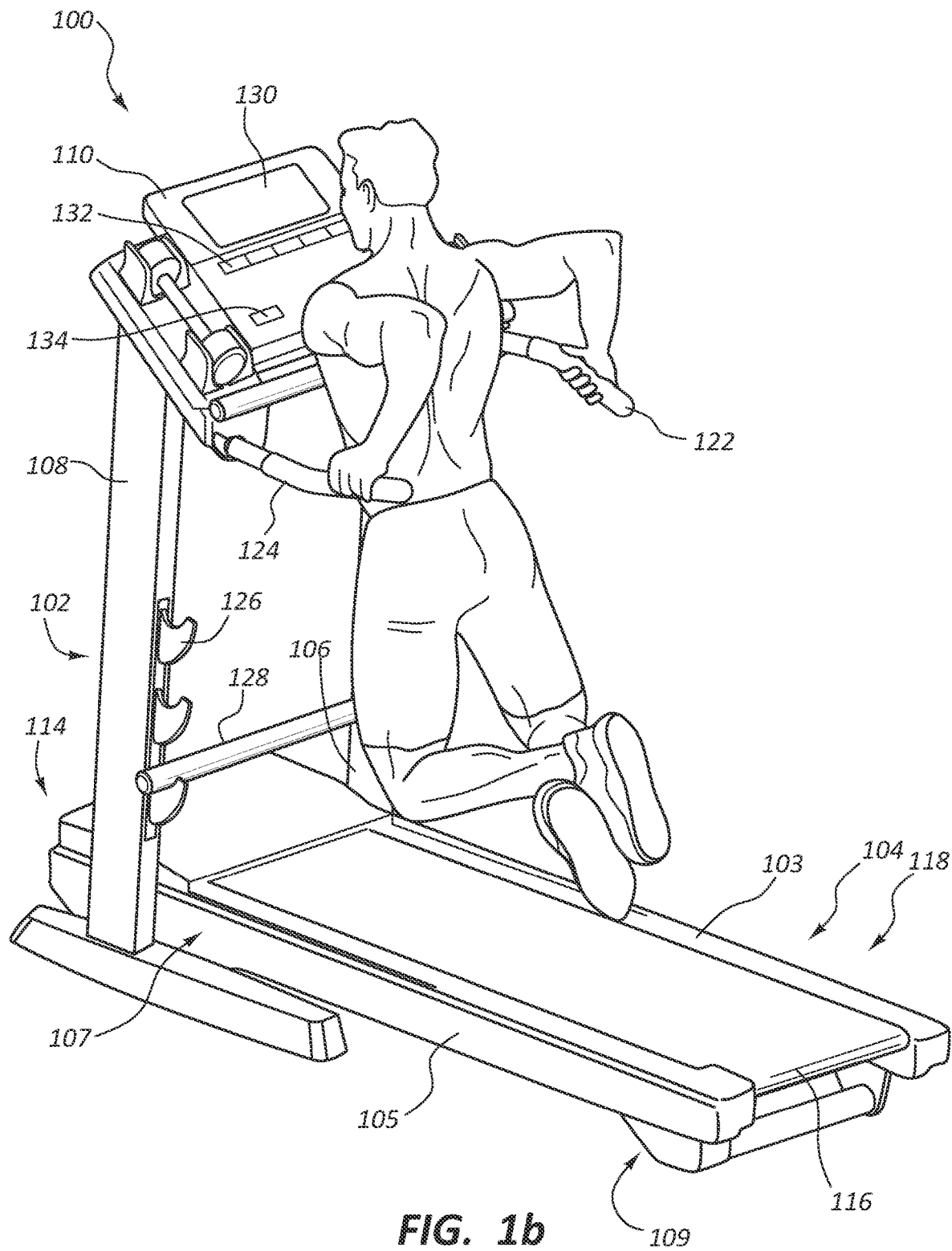
FIG. 1b illustrates a perspective view of an example of treadmill in accordance with the present disclosure.

FIG. 1b depicts a treadmill 100 with a frame 102, and an exercise deck 104 connected to the frame. The frame 102 includes a first post 106 and a second post 108. A console 110 is supported by the first post 106 and the second post 108.

The exercise deck 104 comprises a first rail 103 and a second rail 105. A first pulley is located in a front section 114 of the treadmill 100 and proximate a first end 107 of both the first and second rails, 103, 105. Also, a second pulley 116 is located in a rear section 118 of the treadmill 100 and proximate a rear end 109 of both the first and second rails, 103, 105. A tread belt 120 is disposed between the first pulley and the second pulley 116.

A first handle 122 is movably attached to the frame 102 on a first side of the treadmill 100, and a second handle 124 is movably attached to the frame 102 on a second side of the treadmill 100. In this example, the first and second handles 122, 124 are in a first orientation that is aligned with a length of the exercise deck 104. In such a first orientation, the first and second handles 122, 124 are positioned within a region that is above the exercise deck 104. In this example, the first and second handles 122, 124 are spaced approximately a human body width apart. Also, multiple bar catches 126 are incorporated into each of the first post 106 and the second post 108. Such bar catches 126 may be used to support a push-up bar 128.

The console 110 includes a display 130 and at least one input mechanism 132. Such an input mechanism 132 may be used to control a parameter of the treadmill 100 or record a condition during the performance of an exercise on the treadmill 100.

Further, the treadmill 100 includes at least one repetition sensor 134 that can count the number of repetitions of an exercise performed by the user. For example, the repetition sensor may be able to count the number of push-ups performed by the user with the push-up bar 128 or the number of body weight exercises performed by the user with the first and second handles 122, 124.

Figure 2:
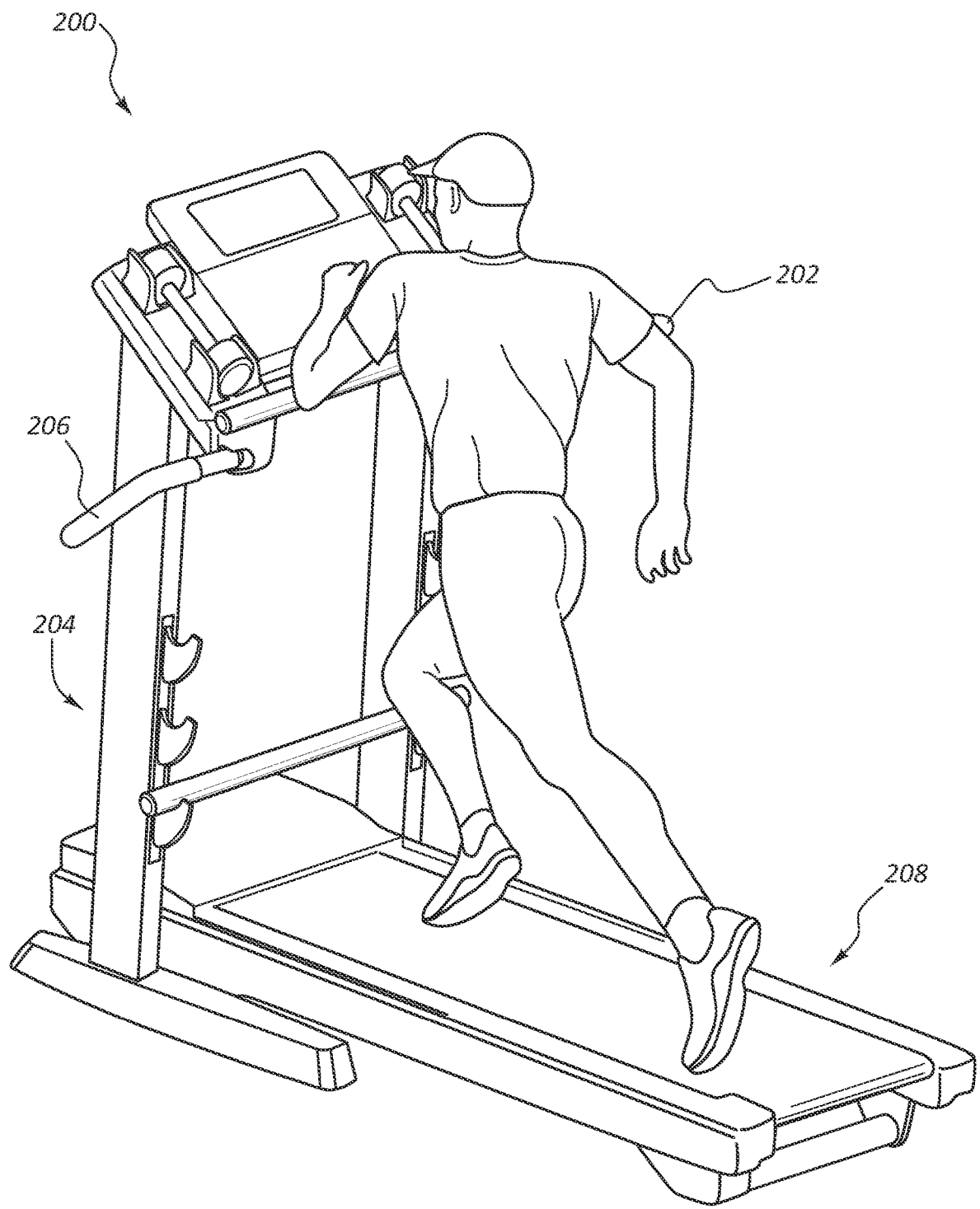
FIG. 2 illustrates a perspective view of an example of a treadmill in accordance with the present disclosure.

FIG. 2 depicts an example of a treadmill 200 with a first handle 202 movably attached to the treadmill's frame 204 and a second handle 206 movably attached to the treadmill's frame 204. The first and second handles 202, 206 are attached to the frame at a human body width apart from one another. In this example, the first and second handles 202, 206 are rotated outwardly from a center of the treadmill 200. In such an orientation, the first and second handles 202, 206 are transverse to the length of the exercise deck 208.

Figure 3:
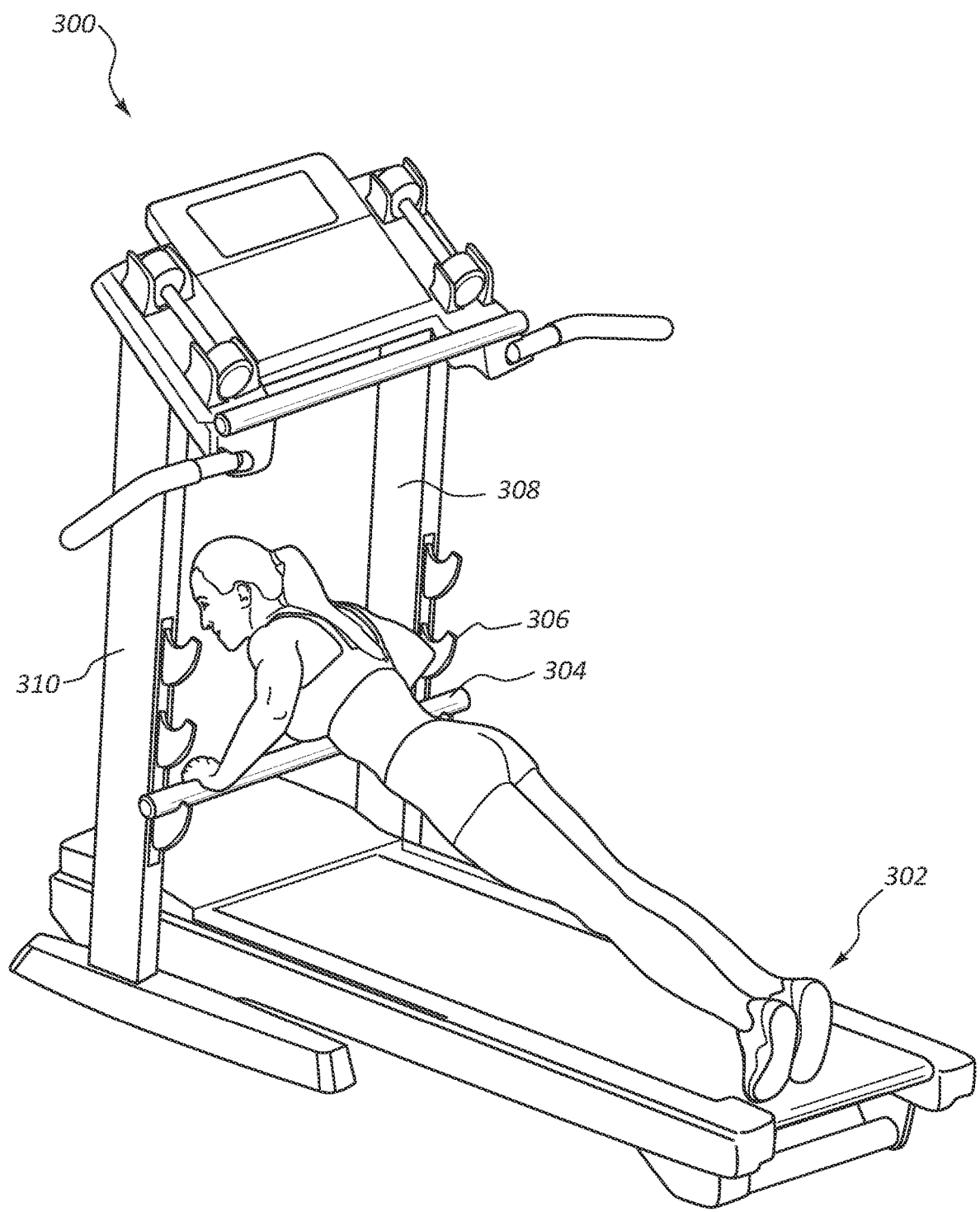
FIG. 3 illustrates a perspective view of an example of a treadmill in accordance with the present disclosure.

FIG. 3 depicts an example of a treadmill 300 of a user performing an anaerobic exercise on the exercise deck 302 with the push-up bar 304. The push-up bar 304 is secured to the catches 306 incorporated into the first post 308 and the second post 310 of the treadmill's frame 312.

Figure 4:
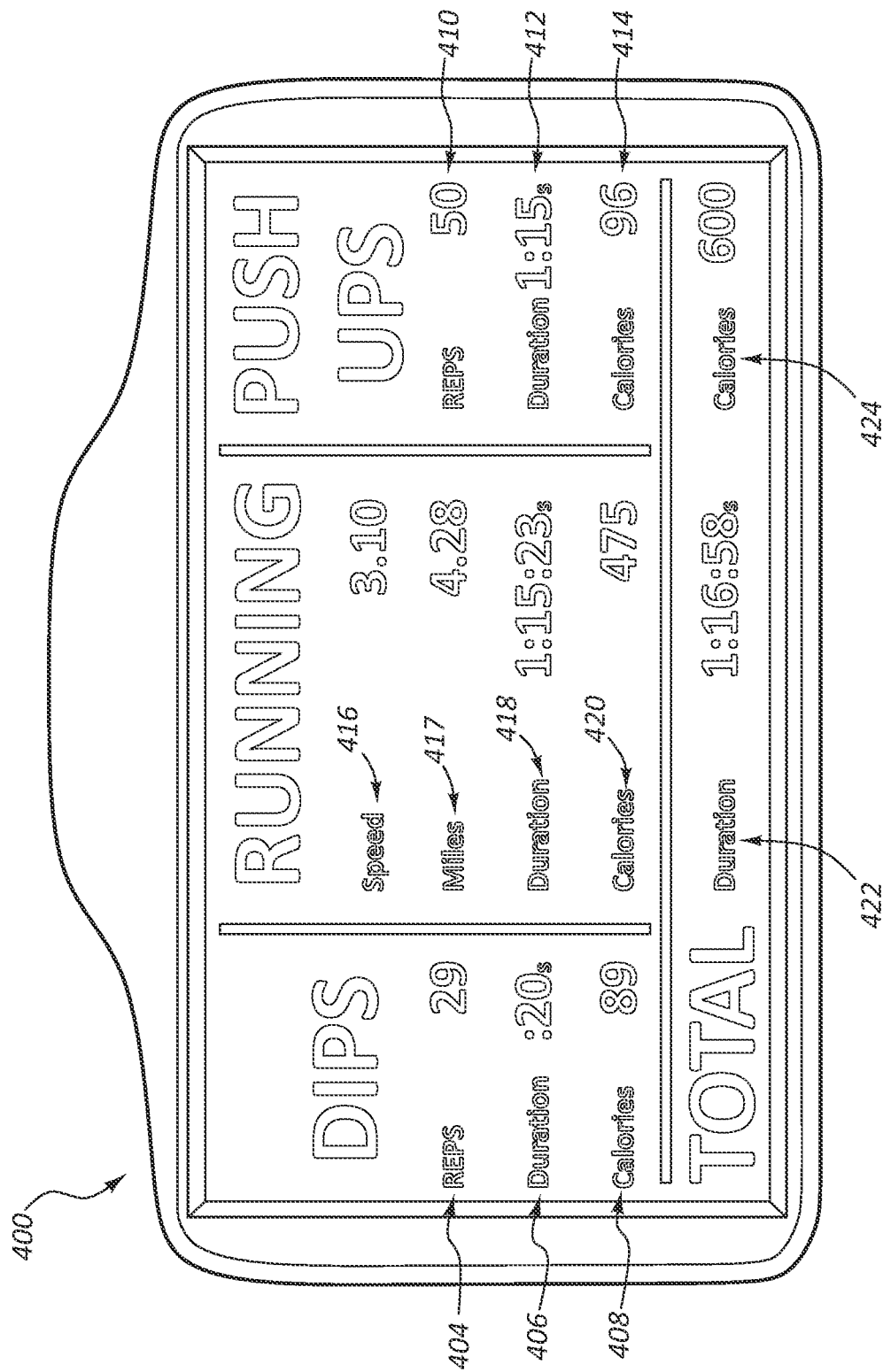
FIG. 4 illustrates a view of an example of a display of a treadmill in accordance with the present disclosure.

FIG. 4 depicts an example of a display 400 in a treadmill. In this example, the display 400 presents to the user a dip repetition number 404, a dip time duration 406, a dip calorie burn 408, a push-up repetition number 410, a push-up time duration 412, a push-up calorie burn 414, a running speed 416, a running distance 417, a running time duration 418, a running calorie burn 420, a total workout duration 422, and a total calorie count 424.

Figure 5:
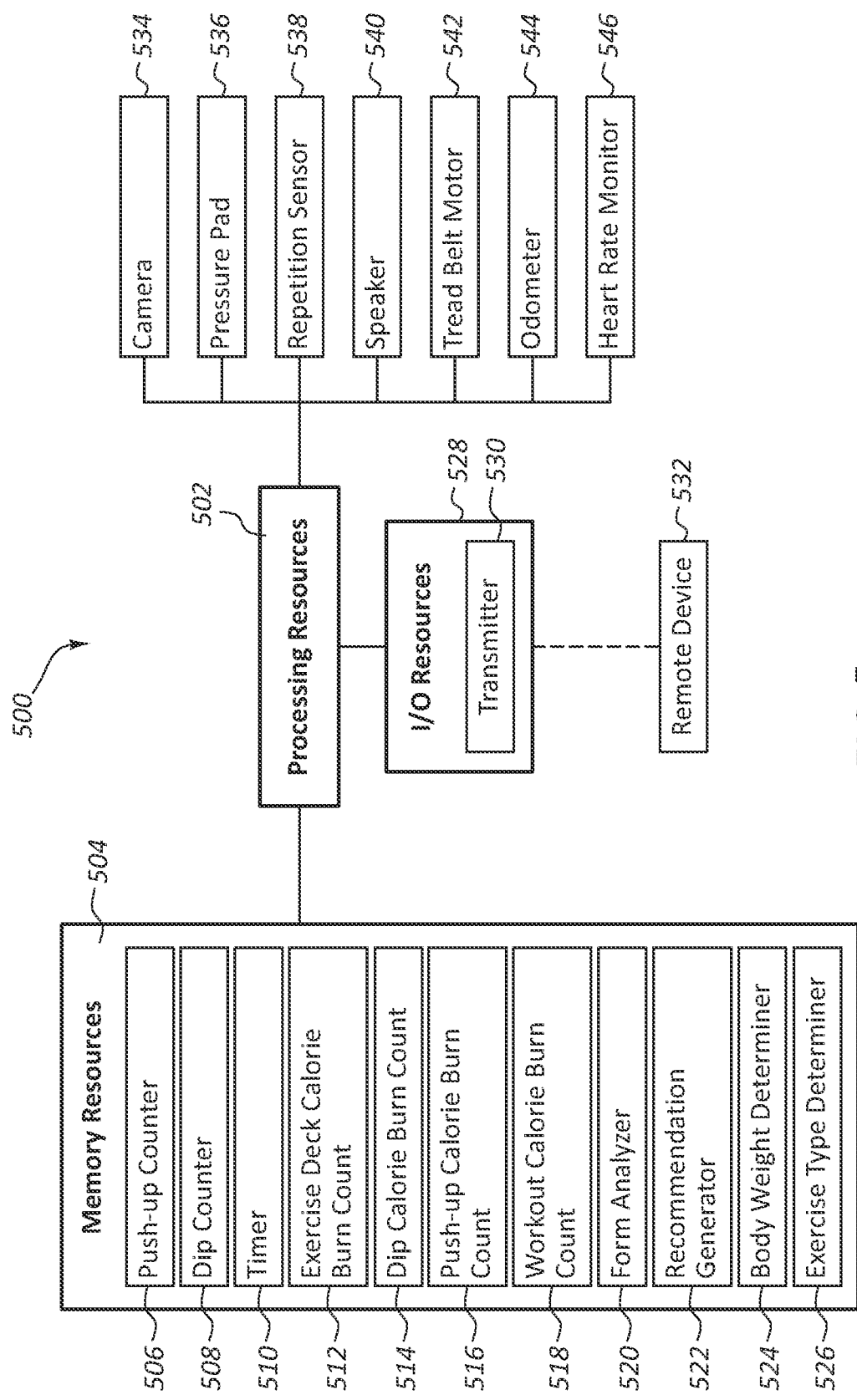
FIG. 5 illustrates a block diagram of an example of a treadmill in accordance with the present disclosure.

FIG. 5 depicts a block diagram of components of an example of a treadmill system 500. In this example, the treadmill system 500 includes processing resources 502 and memory resources 504. The memory resources 504 include a push-up counter 506, a dip counter 508, a timer 510, an exercise deck calorie burn count 512, a dip calorie burn count 514, a push-up calorie burn count 516, a workout calorie burn count 518, a form analyzer 520, a recommendation generator 522, a body weight determiner 524, and an exercise type determiner 526.

The processing resources 502 are also in communication with I/O resources 528, which includes a transmitter 530. The I/O resources may be in communication with a remote device 532.

In illustrated example, the processing resources 502 are also in communication with a camera 534, a pressure pad 536, a repetition sensor 538, a speaker 540, a tread belt motor 542, an odometer 544, and a heart rate monitor 546.

Figure 6:
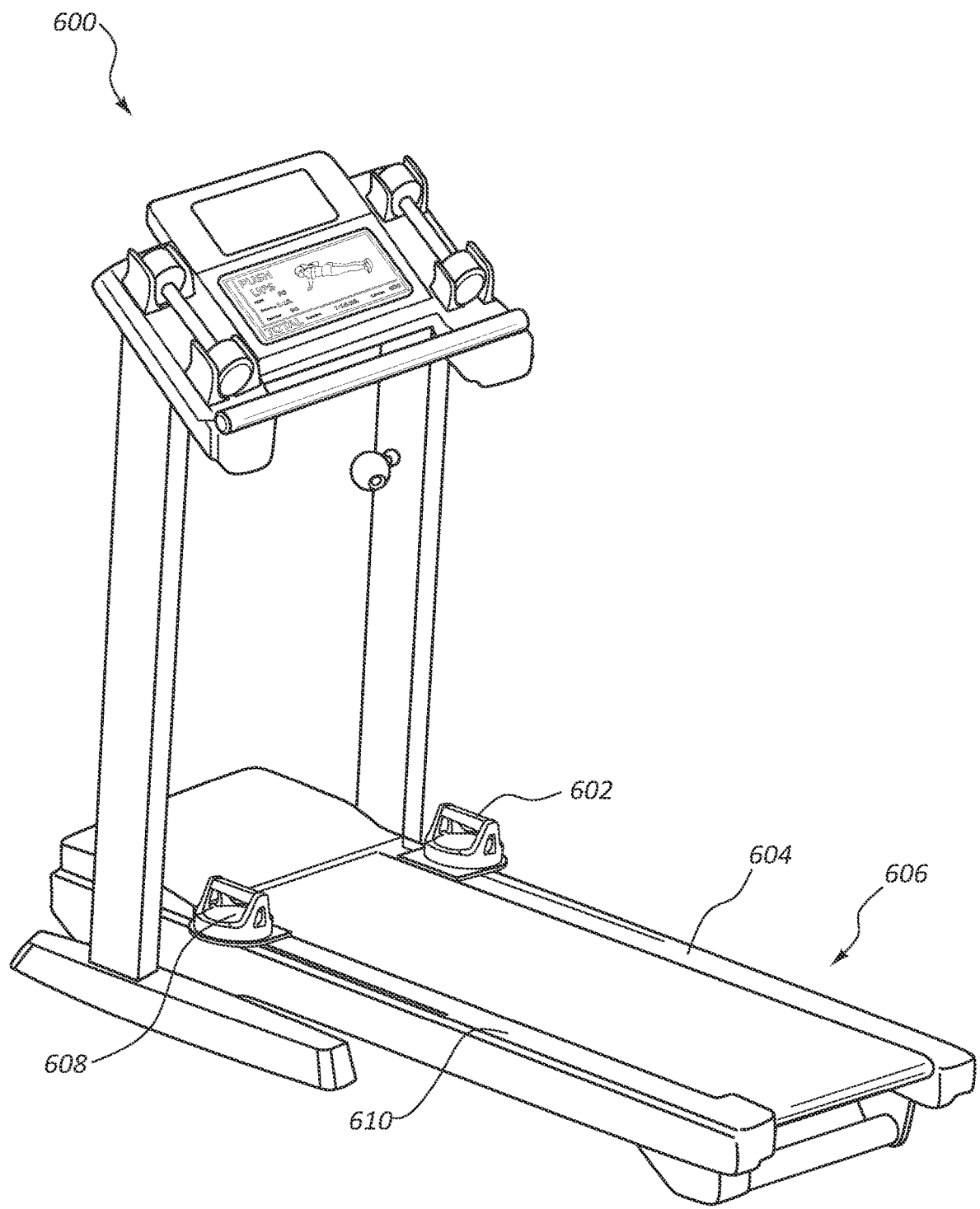
FIG. 6 illustrates a perspective view of an example of a treadmill in accordance with the present disclosure.

FIG. 6 depicts an example of a treadmill 600 with a first push-up bar 602 connected to a first side rail 604 of the exercise deck 606, and a second push-up bar 608 connected to a second side rail 610 of the exercise deck 606. The first and second push-up bars 602, 608 are spaced a human body width apart. A user may grasp the first push-up bar 602 with a first hand and grasp the second push-up bar 608 with a second hand while the user's feet are supported on the exercise deck 606 to perform a push-up exercise.

Figure 7:
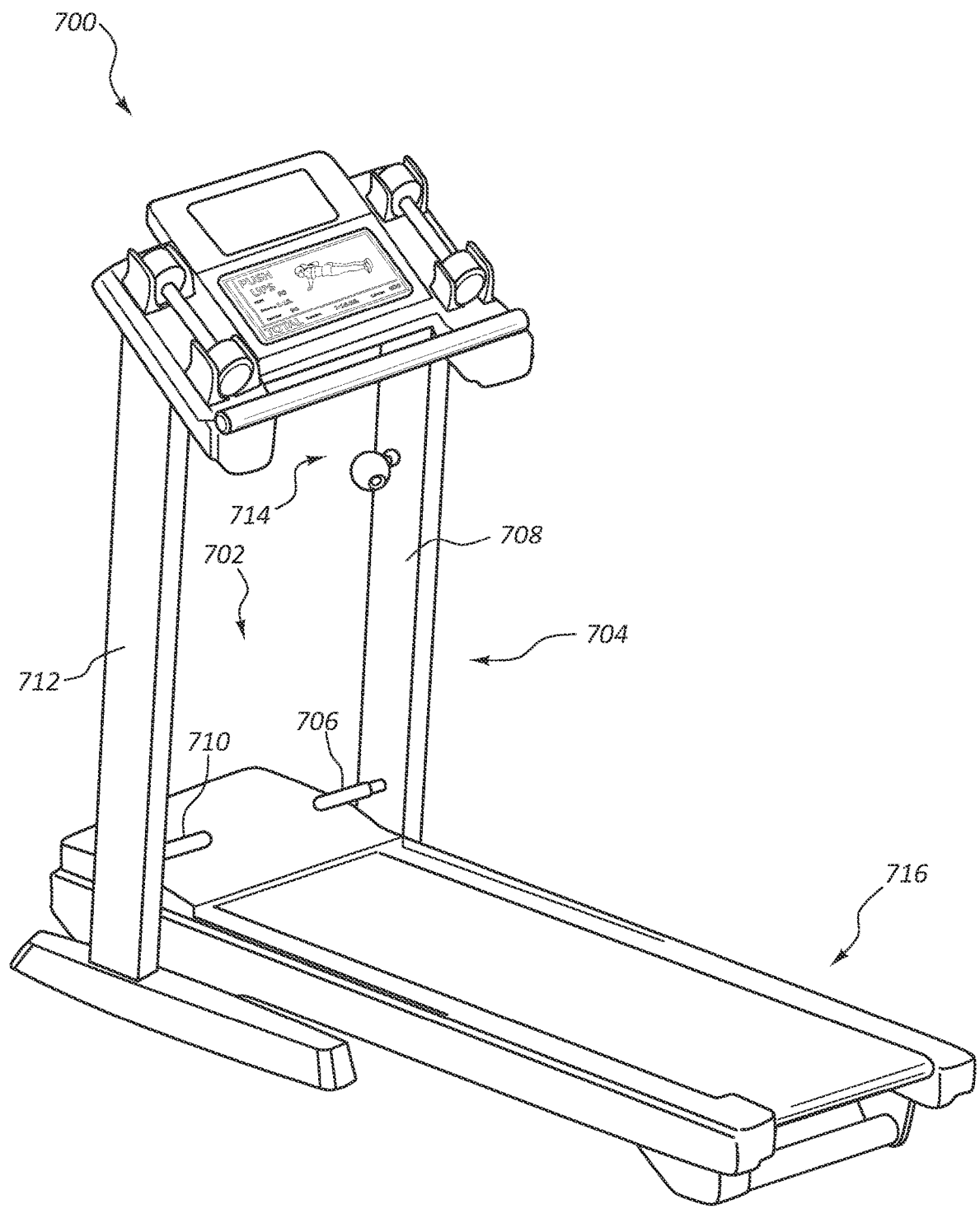
FIG. 7 illustrates a perspective view of an example of a treadmill in accordance with the present disclosure.

FIG. 7 depicts an example of a treadmill 700 with a discontinuous push-up bar 702 attached to the treadmill's frame 704. In this example, the discontinuous push-up bar 702 comprises a first push-up handle 706 connected to a first post 708 of the treadmill's frame 704 and a second push-up handle 710 connected to a second post 712 of the treadmill's frame 704. The first and second push-up handles 706, 710 are oriented to extend towards one another from inside surfaces 714 of the first and second posts 708, 712 and are spaced a human body width apart. A user may grasp the first push-up handle 706 with a first hand and grasp the second push-up handle 710 with a second hand while the user's feet are supported on the exercise deck 716 to perform a push-up exercise.

Figure 8:
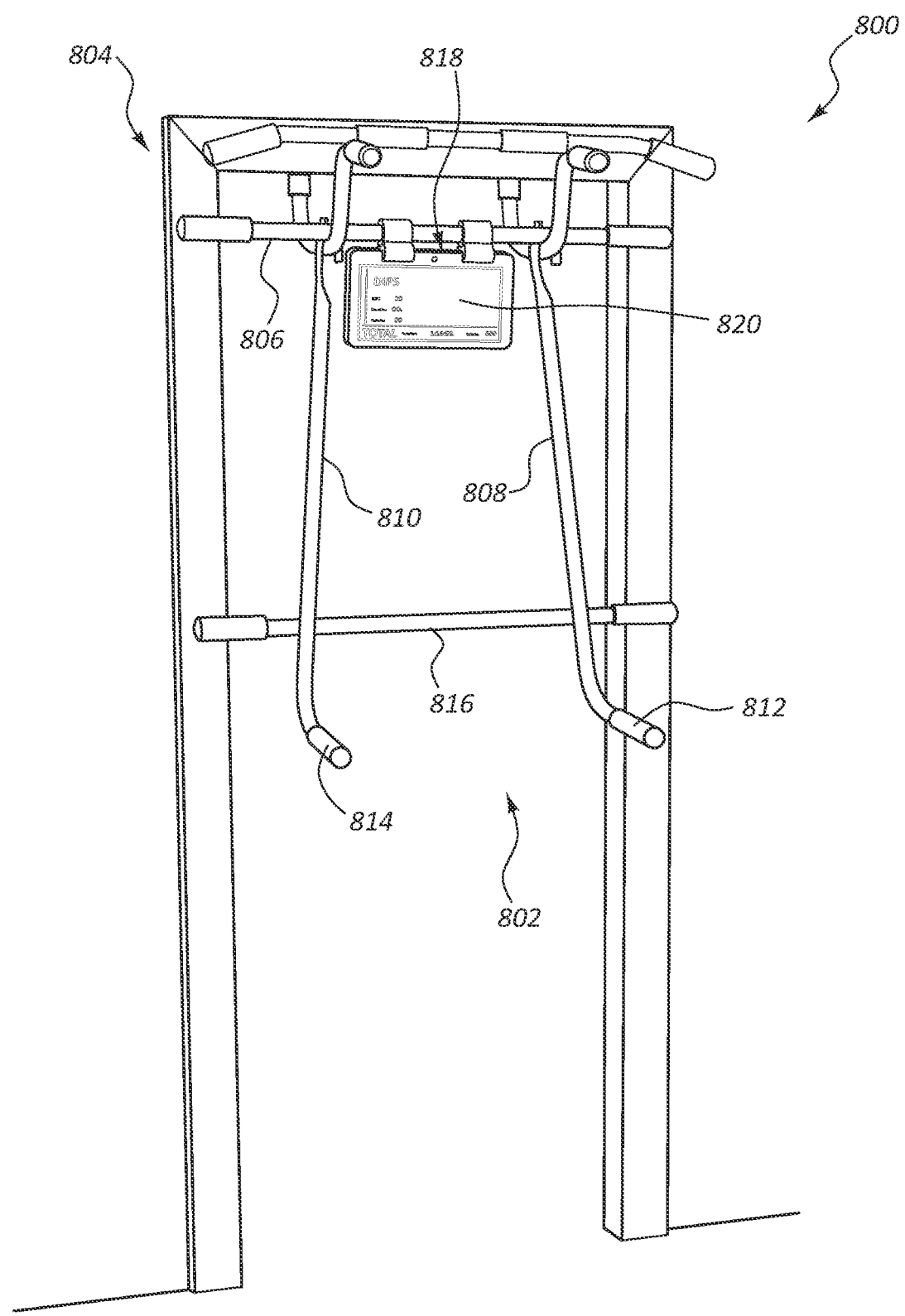
FIG. 8 illustrates a perspective view of an example of a body weight exercise device in accordance with the present disclosure.

FIG. 8 depicts an example of a body weight exercise device 800. In this example, the body weight exercise device 800 includes a frame 802 that has a connection 804 to a door way. However, in other examples, the body weight exercise device 800 may be attached to another structure, such as a wall, building, truss, I-beam, and so forth. The connection 804 may include a beam (not shown) that rests on the upper edge of the door frame and a first cross bar 806 that abuts against the front of the door frame. With the beam resting on the backside of the door frame and the first cross bar abutted against the front of the door frame, the body weight exercise device 800 can securely suspend a user's body weight. A first extension member 808 and a second extension member 810 position a first handle 812 and a second handle 814 below the connection 804 to provide the user hand grips. A second cross bar 816 may be used to provide additional stability.

A camera 818 is incorporated into the body weight exercise device 800 that is angled to detect the movements of the user during the performance of an exercise. The body weight exercise device 800 also includes a display screen 820 where the body weight exercise count can be displayed to the user. In some examples, the number of calories burned by the performance of the body weight exercises is also calculated and presented to the user in the display screen.

Figure 9:
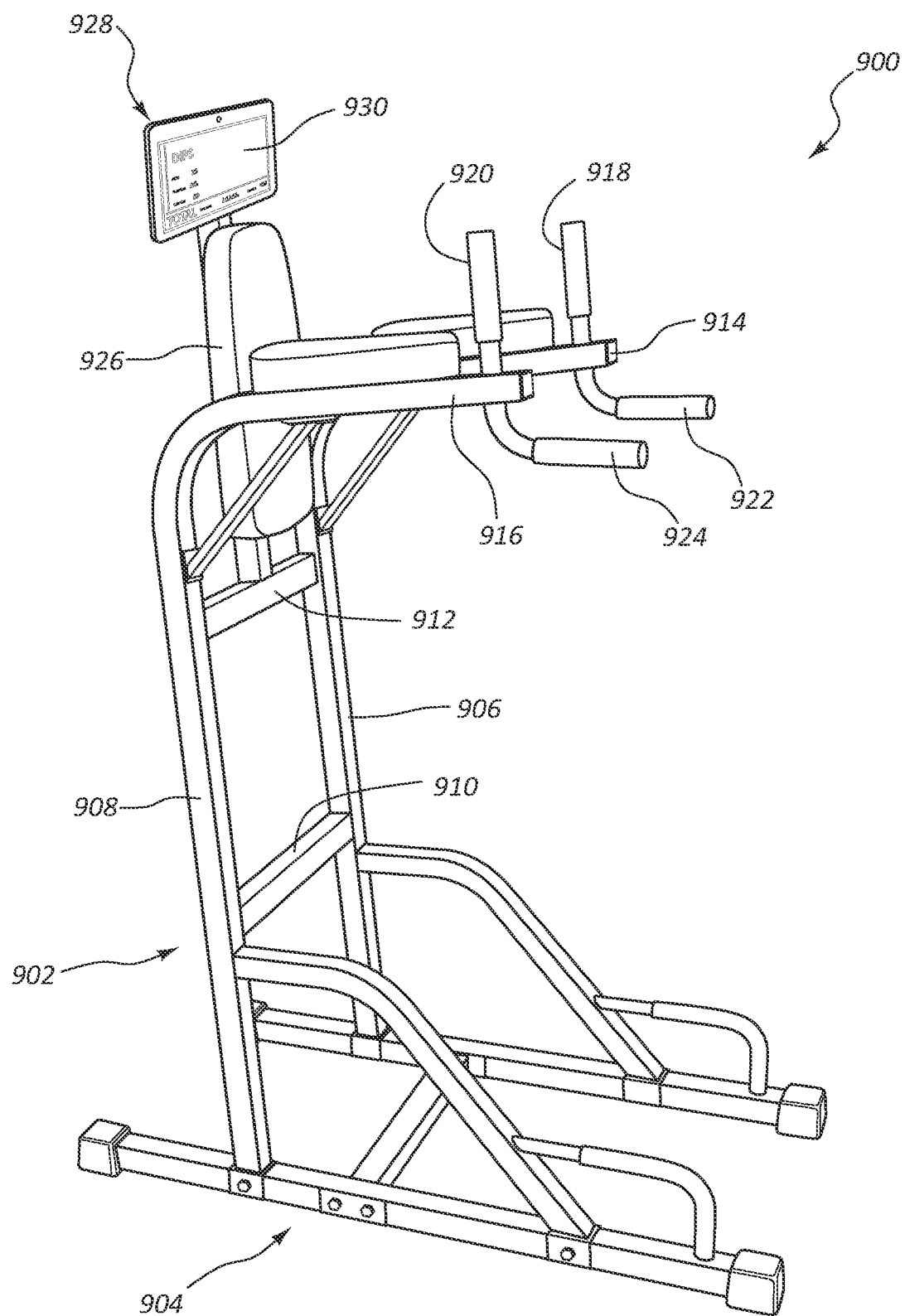
FIG. 9 illustrates a perspective view of an example of a body weight exercise device in accordance with the present disclosure.

FIG. 9 depicts an example of another type of body weight exercise machine 900. In this example, the body weight exercise machine 900 includes a frame 902 that is supported by a base 904. The frame 902 includes a first upright frame post 906 and a second upright frame post 908. A lower cross bar 910 and an upper cross bar 912 are connected to both the first and second upright frame posts 906, 908 to add stability to the body weight exercise machine 900. Additionally, a first support arm 914 is attached to the first upright frame post 906, and a second support arm 916 is attached to the second upright frame post 908. A first handle bar 918 is attached to the first support arm 914 in a transverse orientation with respect to the first support arm 914, and a second handle bar 920 is attached to the second support arm 916 in a transverse orientation with respect to the second support arm 916. Additionally, A third handle bar 922 is attached to the first support arm 914 in an aligned orientation with respect to the first support arm 914, and a fourth handle bar 924 is attached to the second support arm 916 in an aligned orientation with respect to the second support arm 916. A back rest 926 is attached to the upper cross bar 912 to provide stability to the user in the performance of some body weight exercises, such as leg lifts.

A user may grasp the third and fourth handle bars 922, 924 to perform a first type of body weight exercise, such as a dipping exercise. The user may also grasp the first and second handle bars 918, 920, rest his or her arms on the first and second support arms 914, 916, and position his or her back against the back rest 926 to perform another type of body weight exercise, such as leg lifts, knee lifts, or another type of exercise.

The body weight exercise machine includes at least one camera 928 to count the number of body weight exercises that are performed by the user. Additionally, a display screen 930 is also included in the body weight exercise machine 900 to display the body weight exercise count and the associated calorie burn.

General Description of the Invention

In general, the invention disclosed herein may provide the user with an exercise device that allows the user to build strength. Such exercise devices may be incorporated into a treadmill. For example, a dipping station or a push-up station may be incorporated into the treadmill. In such an example, sensors incorporated into the treadmill may be able to track the strength exercises. For instance, the sensors may be able to count the number of times that a user performs a dipping exercise or a push-up exercise. In some examples, such sensors may be incorporated into exercise devices that do not include an exercise deck. For example, a body weight exercise device (i.e. a dipping station) may include sensors that track the repetitions of a dipping exercise and a display screen that presents the repetition number to the user. In some instances, the display screen may also present the number of calories burned by performing the dipping exercise or other type of body weight exercise.

In some examples, the treadmill includes an exercise deck that includes a tread belt that spans between a front pulley at a front end of the treadmill and a rear pulley at a rear end of the treadmill. In some examples, one of the front pulley or the rear pulley is driven by a motor, which causes the tread belt to rotate about the front and rear pulleys. In some examples, a top surface of the tread belt moves from the front pulley to the rear pulley. The speed of the tread belt can be controlled by the user or an exercise program at a pace that the user desires to walk or run. In other examples, the speed of the tread belt may be paced for riding a bicycle or another type of self-propelled exercise device on the exercise deck.

As indicated above, the tread belt is rotated by a motor in some examples. In such an example, a motor may be attached to either of the first pulley, the second pulley, or a transmission component that connects to either the first pulley or the second pulley. As the motor rotates, the motor causes the connected pulley to also rotate. The friction between the connected pulley and the tread belt causes the tread belt and the other pulley to rotate as well. The user can adjust the speed of the tread belt though an input mechanism that sends commands to the motor to adjust the motor's speed. In alternative examples, the tread belt is moved by the user. In such examples, the foot impacts imparted to the tread belt cause the tread belt to rotate. A flywheel attached to either the first pulley or the second pulley may store at least a portion of the inertia of the tread belt's movement to help maintain the tread belt's speed at a relatively consistent speed as the user drives the rotation of the tread belt.

Further, in some examples, the treadmill may include a console that includes input devices to control various aspects of the treadmill. In some cases, the console is supported at a front end of the exercise deck with a first frame post connected to a first side of the treadmill and a second frame post connected to a second side of the treadmill.

While any appropriate type of console may be used with the treadmill, the console may include a display, at least one operations controller, a stop input, speakers, physiological sensors, timers, clocks, other features, or combinations thereof. The display may be used to present videos, scenery, entertainment, images, clocks, physiological conditions of the user, touch screen buttons, other information, or combinations thereof. The operations controller may be used to control various operating parameters of exercises performed on the treadmill. Such operating parameters may include the side to side tilt of the exercise deck, the incline of the exercise deck, the speed of the tread belt, the volume of the speakers, image characteristics of the display, the use of the timers, the operation of the physiological sensors, or other functions. The operations controller may be controlled with an input mechanism such as a push button, a touch screen icon, a lever, a dial, a switch, a microphone, a hand gesture camera, another type of input mechanism, or combinations thereof.

The physiological sensors may track physiological information about the user such as the user's heart rate, blood pressure, oxygen saturation level, pulse, respiration, muscle condition, or other physiological conditions. In some examples, such sensors are incorporated into the console. However, in other examples, such physiological sensors are incorporated into one of the first and second arm rests. The physiological sensors may be used to monitor the health of the user which may assist the user in planning future workouts, in maintaining a target health condition during the workout, in calculating an energy expenditure value representing the amount of energy that the user expended during the workout, in performing other functions, or combinations thereof. Generating such an energy expenditure value may take into account the user's weight, age, height, gender, body composition, other personal information, or combinations thereof.

The processes for calculating the energy expenditure may be in communication with a remote device, which has access to personal information about the user. For example, the remote device may include a profile of the user which includes the user's age, weigh, height, gender, body composition, health conditions, other personal information, or combinations thereof. In some cases, the remote device includes a mobile device, a laptop, a remote computer, a server, a computing device, a data center, another type of device, or combinations thereof. Such profile information may be available to the user through an iFit program available through www.ifit.com and administered through ICON Health and Fitness, Inc. located in Logan, Utah, U.S.A. An example of a program that may be compatible with the principles described in this disclosure is described in U.S. Pat. No. 7,980,996 issued to Paul Hickman. U.S. Pat. No. 7,980,996 is herein incorporated by reference for all that it discloses. However, such profile information may be available through other types of programs. For example, such information may be gleaned from social media websites, blogs, public databases, private databases, other sources, or combinations thereof. In yet other examples, the user information may be accessible through the treadmill. In such an example, the user may input the personal information into the treadmill before, after, or during the workout.

An incline mechanism may be used to control the front to rear slope of the exercise deck. In the cases, the slope of the exercise deck is relatively flat. However, in other examples the incline mechanism may raise or lower a front section of the treadmill to create a different slope. Any appropriate type of incline mechanism may be used to raise and/or lower either a front section or a rear section of the treadmill. Further, any appropriate type of slope may be achieved with the incline mechanism. In some examples, the front to rear slope of the exercise deck may be negative 15.0 degrees where the front section is lower than the rear section. In yet other examples, the front to rear slope may be a positive 45.0 degrees where the front section is higher than the rear section. In other examples, the front to rear slope angle is between negative 45.0 degrees and positive 45.0 degrees. Further, in some embodiments, the exercise deck is capable of changing its side-to-side tilt angle.

In some cases, the treadmill incorporates a strength device. For example, the treadmill may include a first handle and a second handle directly or indirectly attached to the treadmill's frame that are spaced a human body width apart. In some cases, the first handle is attached proximate the first post of the treadmill's frame, and the second handle is attached proximate the second post of the treadmill's frame. The handles may be movably attached to the treadmill such that the handles can be moved to at least a first orientation and a second orientation. In the first orientation, the handles may be aligned with the length of the exercise deck such that the handles are above the exercise deck. In the second orientation, the handles may be moved outwardly away from a centerline of the exercise deck. In some examples, the handles are slidably connected to the treadmill frame such that the handles remain aligned with the length of the exercise deck's length as the handles move away from the centerline of the exercise deck. In the second orientation, the handles may be moved far enough out that they are no longer above the exercise deck. In alternative examples, the handles may be rotationally connected to the treadmill. In such an example, the handles may pivot away from the centerline of the exercise deck into the second orientation and be positioned in a transverse orientation to the exercise deck's length.

When the handles are in the first orientation, the user may grasp the handles with his or her hands and raise himself or herself off of the exercise deck. The user may then bend his or her knees and lower his or her body downward towards exercise deck without loading the user's weight back to the exercise deck. Often, in this lowered position, the user's elbows are raised towards the user's head and the user's pectoral muscles are stretched. To raise the user to an upper position, the user engages both his pectoral muscles and arm muscles to finish a repetition of a dip exercise. With the handles in the second orientation, the handles are moved out of the way so that they do not interfere with the user performing an aerobic exercise on the exercise deck, such as running, walking, or cycling.

A repetition sensor may be incorporated into the treadmill to count the number of times that the user performs a dipping exercise. In some examples, the repetition sensor can detect when the user is in the lowered position, the upper position, or transitioning there between. Each time that the repetition sensor detects the user's body is in the predetermined position, the repetition sensor can record the count that may result in a counter incrementing the count by one. Such a count may be presented to the user in a display screen incorporated into the treadmill. In other examples, the count may be presented to the user through an audible counter or another mechanism.

Any appropriate type of repetition sensor may be used in accordance with the principles described in the present disclosure. For example, the repetition sensor may be a camera that can detect the user's position or at least some of the positions that the user is in during the performance of the dipping exercise or another body weight exercise. Such a camera may be a camera that operates in the visible light portion of the electromagnetic spectrum. In such an embodiment, the camera may utilize an image recognition program that determines the position of the user based on the color values in the camera's pixels. In another example, the camera operates in the infrared portion of the electromagnetic spectrum. In other examples, the camera is a distance camera that emits a signal and measures the time of flight for a reflection of the signal to return.

In another example, the repetition sensor includes a pressure gauge, strain gauge, or another type of gauge that is in communication with the handles. In such an embodiment, the varying weight loads applied to the handles during the performance of the exercise can be analyzed to determine the number of body weight exercises performed by the user. For example, the forces on the handles during the upward movement of a dipping exercise may exhibit a greater load than when the user is in a resting position or moving in the downward direction. Thus, the expected load increases experienced by the handles can be correlated to the upward movement of the dipping exercise. Accordingly, each time the load increases to a level expected during the performance of a dipping exercise, the counter can be caused to increment the count by one.

In some examples, the sensors may be used as a primary sensor for determining the number repetitions performed by the user. However, in other examples, multiple sensors may be used to determine the number of the repetitions performed by the user or to collect other types of information about the user's performance. For example, a camera may be used as a sensor for collecting repetition information about the user's performance, and a strain gauge may be used to verify that the readings received through the camera appear to be accurate. In some examples, a first camera may be used to verify the accuracy of another camera at a different angle or have a different feature that can corroborate the information gathered from the second camera.

While the examples above have been described with the user performing a dipping exercise with the handles incorporated into the treadmill, any appropriate type of body weight exercise may be performed with the handles. For example, the user may use the handles to perform a leg lift exercise, a knee lift exercise, a dipping exercise, a modified push-up, a modified pull-up, a modified row, another type of body weight exercise, or combinations thereof.

In some examples, the treadmill may also incorporate a push-up bar. The push-up bar may be incorporated into the treadmill in any appropriate manner in accordance with the principles described in the present disclosure. In one example, both the first post and the second post of the treadmill's frame include at least one catch on which an end of a push-up bar can be supported. The catch may be a protrusion from the treadmill post that is made of a material that can support the weight of a push-up bar and the loads applied to the push-up bar. Such catches may be angled slightly upward to cause the push-up bar to roll or otherwise move towards the treadmill's frame posts. In some embodiments, the catches are removably attached to the frame posts. Alternatively, the catches are permanently attached to the frame posts. Each post may include at least one catch that is aligned with another catch on the other post. With the catches aligned, each catch may support one end of the push-up bar. One advantage to securing the push-up bar to the frame posts through the catches is that the push-up bar is easily removed. In some examples, it may be advantageous to move the push-up bar when performing a running or walking exercise on the exercise deck. In other examples, the push-up bar may remain in place without interfering with the performance of a walking or running exercise. Further, each post may have multiple catches with each catch per post located at different elevations. In such an example, the height of the push-up bar may be changed as desired by the user.

In some situations, it may be desirable to remove the push-up bar from the frame posts when the exercise deck is being inclined during the running or walking exercise performed on the exercise deck. In such an example, the user may manually remove the push-up bar. In other examples, the treadmill may include a mechanism that moves the push-up bar automatically in response to instructing the exercise deck to incline. For example, the catches may move up on a rack and pinion assembly, a screw motor, a hydraulic mechanism, another type of mechanism, or combinations thereof.

In alternative examples, the push-up bar may be permanently attached to the posts. In such an example, the ends of the push-up bar may be screwed or otherwise fastened to the posts. Alternatively, the push-up bar may be welded or integrally formed with the posts. In some cases, the push-up bar is discontinuous. In such an example, a first handle of the push-up bar can be incorporated into the first post and project inward towards the second post, and a second handle of the push-up bar can be incorporated into the second post and project inward towards the first post. In some instances, the distance between the first and second push-up bar handles is sufficient to allow a user to drop between the push-up bar handles while performing push-up exercises.

In yet another example, the push-up handles may be incorporated into the exercise deck. In such an example, a first push-up bar may be incorporated into a first rail of the exercise deck, and a second push-up bar may be incorporated into a second rail of the exercise deck. Each of the first and second push-up bars may be elevated a distance off of the surface of the exercise surface. In this example, when performing push-ups the user may face the surface of the exercise deck while grasping the first push-up bar with his or her first hand and grasping the second push-up bar with his or her second hand.

As described above, the repetition sensor may be used to count the number of push-up exercises executed by the user with the push-up bar. Such repetition sensors may include cameras, strain gauges, pressure gauges, other types of sensors, or combinations thereof.

The number of push-ups, the number of dips, and the number of other types of body weight exercises may be presented to the user in a display incorporated into the treadmill or other type of exercise machine. In some examples, such a display screen may be incorporated into the console. Alternatively, the display screen may be incorporated into an area of the exercise machine where the user can view the display screen during the performance of the strength exercises. In some examples, redundant display screens may be incorporated into the exercise machine so that the user can view the exercise counts while performing different types of exercises.

The sensor may have the intelligence to distinguish between different types of exercises. For example, the sensor may be able to determine when the user is performing an exercise with the handles verses the push-up bar. Further, the sensor may be able to distinguish between when the user is performing different types of exercises with the handles. In such an example, the camera may be able to track the location, direction, and speed of the user during the exercise. For example, if the user is using the handles to perform a modified row, the user grasps the handles with both hands, but the user will be facing upwards. In some examples, the sensor may be able to determine based on the pixel readings that the user is facing upwards and draw a conclusion that the user is performing a row exercise. As the user executes the row exercises, the user's body will alternate between a lower position and a higher position. In such an example, the lower position is proximate the surface of the exercise deck and the upper position is proximate the height the handles. Such lower positions are different than the lower positions of the user during a modified push-up exercise, a dipping exercise, a leg lift exercise, a knee lift exercise, or another type of exercise. Thus, in some examples, the sensor may determine the type of exercise performed by the user based on just the lowered and upper positions. In yet other examples, the sensor may determine the type of exercise based on the angle of the user. In some examples, multiple factors, such as the user's facing direction, angle of the user's body, the lower position, the upper position, and so forth are collectively analyzed to determine the type of exercise being performed by the user. In other examples, just one of the factors may be dispositive for determining the type of exercise being performed by the user.

In addition to knowing the type of exercise, a system incorporated into the exercise machine may have other information about the user. For example, this additional information may include the user's age, gender, weight, height, body composition, health risks, health factors, injuries, and so forth. This information may be used to determine the amount of force needed to move the user during the performance of the exercise being executed by the user. Thus, the system may assign a calorie value to each repetition of the exercise being performed by the user. In some examples, the calorie burn count per exercise is merely the repetition number multiplied by a consistent calorie number calculated based on just the user's personal information. In other examples, the sensor can record and track other conditions that may modify the calorie burn count per repetition. For example, the sensor may record the user's angle in the performance of the exercise. Performing a push-up at a steeper angle (i.e., push-up bar is secured to the highest catch incorporated in the posts), the user may be burning less calories than when the user is performing a push-up at a lower angle (i.e. push-up bar is secured to the lowest catch incorporated into the posts). In some instances, the camera may record the angle during push-ups or other such exercises and modify the number of calories burned per exercise repetition. In some examples, the speed at which the user executes an exercise may also impact the number of calories burned during the performance of the exercise. In some instances, the sensors can also record the user's speed and calculate a modified calorie burn number per exercise repetition. In yet other examples, the sensor can determine the stroke distance per exercise. For example, when a user is performing a dip, the sensor may track how far down the user traveled and adjust the calorie count when the user either falls short of the predetermined stroke distance or exceeds the predetermined stroke distance.

A camera can record the parameters described above with shape recognition programs that can recognize the user's various body parts and identify the location of each of the identified body parts based on the pixel data. Each frame of the camera may be associated with a timestamp. As the user's body parts move during the exercise, the time stamps can be used to determine the speed at which the body parts moved to determine the speed that the exercise is being executed. Additionally, the angles of the user and facing direction of the user can be determined based on the identified location of the user's body parts.

In examples where the exercise machine is a treadmill, the treadmill may contain programs that determine the number of calories burned by the user during the performance of exercises on the exercise deck (i.e., running or walking). The display may present the exercise types and the associated calorie burn for each of the identified exercise types. In one such example, the display screen includes a repetition number for push-ups associated with a calorie burn number, a repetition number for dips associated with a calorie burn number, and a running time duration associated with a speed and a calorie burn number. Additionally, the display screen may present an overall number of calories burned that totals the calories contributed from each of the push-ups, dips, and running exercises. In some examples, the force exerted by the user during the performance of the exercise may be calculated and presented in the display screen. The force may be determined by considering factors such as the user's body weight, the amount of weight loaded to the user, and the speed at which the user accomplished the exercise.

The system may include a combination of hardware and programmed instructions for executing the functions of the system. In this example, the system includes processing resources that are in communication with memory resources. Processing resources include at least one processor and other resources used to process the programmed instructions. The memory resources represent generally any memory capable of storing data such as programmed instructions or data structures used by the system. The programmed instructions shown stored in the memory resources include a push-up counter, a dip counter, a timer, an exercise deck calorie burn count, a dip calorie burn count, a push-up calorie burn count, a workout calorie burn count, a form analyzer, a body weight determiner, and an exercise type determiner.

Further, the processing resources may be in communication with user information and/or workout environment information that may be stored in the memory resources locally or off site. For example, the processing resources may be in communication with a remote device that stores the user information or workout environment information. Such a remote device may be a mobile device, a cloud-based device, a computing device, another type of device, or combinations thereof. In some examples, the system communicates with the remote device through the mobile device which relays communications between the system and the remote device. In other examples, the mobile device has access to information about the user and/or workout environment. In some cases, the remote device collects information about the user during his or her workout or in general. In one such example, the exercise machine may send information to the remote device indicating the types of exercises performed by the user, the number of calories burned by the user, the average heart rate of the user during the workout, other types of information about the workout, or combinations thereof. An example of a program that may be compatible with the principles described herein includes the iFit program which is available through www.ifit.com and administered through ICON Health and Fitness, Inc. located in Logan, Utah, U.S.A. An example of a program that may be compatible with the principles described in this disclosure are described in U.S. Pat. No. 7,980,996 issued to Paul Hickman. U.S. Pat. No. 7,980,996 is herein incorporated by reference for all that it discloses. In some examples, the user information accessible through the remote device includes the user's age, gender, body composition, height, weight, health conditions, other types of information, or combinations thereof. Further, the workout environment information that may be accessible to the remote device may include humidity data, temperature data, elevation data, atmospheric pressure data, sunlight exposure data, other types of environmental data, or combinations thereof.

The processing resources, memory resources, and remote devices may communicate over any appropriate network and/or protocol through the input/output resources. In some examples, the input/output resources include a transceiver for wired and/or wireless communications. For example, these devices may be capable of communicating using the ZigBee protocol, Z-Wave protocol, BlueTooth protocol, Wi-Fi protocol, Global System for Mobile Communications (GSM) standard, another standard, or combinations thereof. In other examples, the user can directly input some information into the system through a digital input/output mechanism, a mechanical input/output mechanism, another type of mechanism, or combinations thereof. For example, such input mechanisms may be incorporated into the console of the exercise machine or at another location on the exercise machine. In some circumstances, the exercise machine includes multiple sensors. In such an example, each of the sensors may communicate as part of the network described above.

The memory resources may include a computer readable storage medium that contains computer readable program code to cause tasks to be executed by the processing resources. The computer readable storage medium may be a tangible and/or non-transitory storage medium. The computer readable storage medium may be any appropriate storage medium that is not a transmission storage medium. A non-exhaustive list of computer readable storage medium types includes non-volatile memory, volatile memory, random access memory, write only memory, flash memory, electrically erasable program read only memory, magnetic based memory, other types of memory, or combinations thereof.

The push-up counter represents programmed instructions that, when executed, cause the processing resources to count the number of push-ups performed by the user. The dip counter represents programmed instructions that, when executed, cause the processing resources to count the number of dips performed by the user. The push-up counter and the dip counter may receive input from a repetition sensor, a camera, a pressure pad, a strain gauge, another type of sensor, or combinations thereof. Such sensors may analyze multiple factors to determine the user's exercise angle, stroke distance, other parameter, or combinations thereof. The timer represents programmed instructions that, when executed, cause the processing resources to determine the time different between the start and finish of an exercise. In some cases, the timer determines the start and finish of a single repetition or just a portion of a repetition (i.e., just the upward movement of an exercise). In other examples, the time is used to determine the time duration for executing a workout.

The exercise deck calorie burn counter represents programmed instructions that, when executed, cause the processing resources to determine the number of calories burned by the user while performing an exercise on the exercise deck. Such exercises may include walking, running, skipping, cycling, backward running, backward walking, another type of exercise, or combinations thereof. The exercise deck calorie burn counter may determine the calorie count by analyzing factors, such as the user's heart rate, the time duration that the exercise was executed, the user's body weight, age, gender, body composition, other factors, or combinations thereof.

The dip calorie burn counter represents programmed instructions that, when executed, cause the processing resources to count the number of calories burned while performing dip exercises with the exercise machine. The push-up calorie burn counter represents programmed instructions that, when executed, cause the processing resources to count the number of calories burned while performing push-up exercises with the exercise machine. The dip calorie burn counter and the push-up calorie burn counter may analyze a number of parameters that are collected by the sensors incorporated into the exercise machine. For instance, the sensors may collect information such as the angle of the user's body during the exercise, the facing direction of the user's body during the exercise, the speed of exercise execution during the exercise, the user's body weight, age, gender, body composition, other factors, or combinations thereof. These factors may be used to fine tune the calculations for determining the amount of calories burned during the push-up and/or dip calorie burn counters.

The workout calorie burn counter represents programmed instructions that, when executed, cause the processing resources to add up the calorie burn counts from each of the exercises performed during the workout. For example, if the user performed push-ups, dips, and running during the workout, the workout calorie burn counter may add up each of the calories from performing push-ups, dips, and running.

The form analyzer represents programmed instructions that, when executed, cause the processing resources to analyze the form of the user during the performance of a strength exercise. In some embodiments, the form analyze determines the stroke length, the angle of the user's body, and other factors that are useful in the calculation of the calorie burn numbers. However, the form analyzer may also determine whether the user is performing the strength exercises properly. For example, the form analyzer may use a recognition program to determine the locations of the user's hands, feet, head, torso, and so forth. Based on the position and angles of these body parts, the form analyzer may determine that the user is executing the exercise with good form, moderate form, or bad form.

The recommendation determiner represents programmed instructions that, when executed, cause the processing resources to generate a recommendation to the user. In some examples, the recommendation is to improve the user's form. For example, if the user is arching his or her back during push-ups, the recommendation determiner may generate a recommendation to straighten the user's back. The recommendation may be presented to the user in the display screen, through a speaker, through a tactile stimulus, through an electronic message, through another communication mechanism, or combinations thereof. While this example has been described with reference to a specific type of recommendations, any appropriate type of recommendation may be made in accordance with the present disclosure. For example, the recommendation may be to do another repetition, perform an exercise slower, perform an exercise faster, improve posture, to bend knees, lean forward, stop performing an exercise, another type of recommendation, or combinations thereof.

The body weight determiner represents programmed instructions that, when executed, cause the processing resources to determine the user's body weight. In some examples, the body weight determiner consults a data field with a value provided by the user. In some examples, the value is provided from a remote device, such as a user profile that contains the user's weight. In such an example, other types of information about the user may be gleaned from the user profile, such as the user's age, gender, body composition, or combinations thereof. In other examples, a sensor is incorporated into the handles, under the exercise deck, or another location on the treadmill and/or exercise machine to determine the user's weight.

The exercise type determiner represents programmed instructions that, when executed, cause the processing resources to determine the type of exercise being performed by the user. In some examples, the exercise type determiner analyzes the factors described above and determines the type of exercise being performed. In some examples, the user may input into the console or another input mechanism the type of exercise being performed. The user may indicate to the system the type of exercise through any appropriate mechanism. In some examples, the user may speak into a microphone associated with the system to indicate the workout type. In other examples, the user may use a button, a touch screen, a lever, or another input/output mechanism, a remote device, another type of device, or combinations thereof. In other examples, the user is participating in a predetermined program that selects the type of exercises for the user to perform. For example, the user may select a program that instructs the user to perform a number of push-ups, dips, and an aerobic exercise on the exercise deck. In such an example, the exercise type determiner may consult the program to determine which type of exercise that the user is being instructed to perform.

Further, the memory resources may be part of an installation package. In response to installing the installation package, the programmed instructions of the memory resources may be downloaded from the installation package's source, such as a portable medium, a server, a remote network location, another location, or combinations thereof. Portable memory media that are compatible with the principles described herein include DVDs, CDs, flash memory, portable disks, magnetic disks, optical disks, other forms of portable memory, or combinations thereof. In other examples, the program instructions are already installed. Here, the memory resources can include integrated memory such as a hard drive, a solid-state hard drive, or the like.

In some examples, the processing resources and the memory resources are located within the console, the exercise machine, a mobile device, a remote device, another type of device, or combinations thereof. The memory resources may be part of any of these device's main memory, caches, registers, non-volatile memory, or elsewhere in their memory hierarchy. Alternatively, the memory resources may be in communication with the processing resources over a network. Further, data structures, such as libraries or databases containing user and/or workout information, may be accessed from a remote location over a network connection while the programmed instructions are located locally. Thus, the system may be implemented with the exercise machine, a user device, a mobile device, a phone, an electronic tablet, a wearable computing device, a head mounted device, a server, a collection of servers, a networked device, a watch, or combinations thereof. Such an implementation may occur through input/output mechanisms, such as push buttons, touch screen buttons, voice commands, dials, levers, other types of input/output mechanisms, or combinations thereof. Any appropriate type of wearable device may include, but are not limited to glasses, arm bands, leg bands, torso bands, head bands, chest straps, wrist watches, belts, earrings, nose rings, other types of rings, necklaces, garment integrated devices, other types of devices, or combinations thereof.

While the examples above have been described with reference to strength exercise devices being incorporated into a treadmill, the principles described in the present disclosure are also applicable to the body weight exercise devices, such as dipping stations, vertical knee raise stations, pull-up bars, other types of body weight exercise devices, or combinations thereof. For example, a sensor that determines the number of body weight exercises may be incorporated into a body weight exercise device. Such a sensor may gather other information about the workout, such as the angle of the user, the direction that the user is facing, the speed at which the user is exercising, the number and the durations that the user is taking between repetitions, and so on. Further, the body weight exercise device may also include processing and memory resources to use the gathered data to determine the number of calories that the user has burned. In some cases, the number of calories burned is broken down into calories burned by type of exercise. In other examples, just a total of calories burned is determined and presented. In yet other examples, both a calorie break down and the total number of calories burned is presented.

Such calorie information can be presented in a display screen incorporated into the body weight exercise device.

In one example, the body weight exercise device may be a dipping station that includes a frame that has a connection to a doorway. The connection may include a beam that rests on the upper edge of the door frame and a first cross bar that abuts against the front of the door frame. With the beam resting on the backside of the door frame and the first cross bar abutted against the front of the door frame, the body weight exercise device can securely suspend a user's body weight in the air. A first extension member and a second extension member may extend from and position a first handle and a second handle below the connection to provide the user hand grips. A camera may be incorporated into the body dipping station that is angled to detect the movements of the user during the performance of an exercise. The dipping station may also include a display screen where the body weight exercise count can be displayed to the user.

In another example, the body weight exercise machine is a vertical knee raise (VKR) station that includes a frame that is supported by a base on a support surface. The frame includes a first upright frame post and a second upright frame post. Cross bars are connected to both the first and second upright frame posts to add stability to the VKR station. Additionally, a first support arm may be attached to the first upright frame post, and a second support arm may be attached to the second upright frame post. A first handlebar may attached to the first support arm in a transverse orientation with respect to the first support arm, and a second handle bar may be attached to the second support arm in a transverse orientation with respect to the second support arm. Additionally, A third handlebar may be attached to the first support arm in an aligned orientation with respect to the first support arm, and a fourth handle bar may be attached to the second support arm in an aligned orientation with respect to the second support arm. A back rest may be attached to the upper cross bar to provide stability to the user in the performance of some body weight exercises, such as leg lifts.

A user may grasp the third and fourth handlebars to perform a first type of body weight exercise, such as a dipping exercise. The user may also grasp the first and second handlebars, rest his or her arms on the first and second support arms, and position his or her back against the back rest to perform another type of body weight exercise, such as leg lifts, knee lifts, or another type of exercise. Such a VKR station may include at least one camera or another type of repetition sensor to count the number of body weight exercises performed by the user. Additionally, a display screen may also be included in the body weight exercise machine to display the body weight exercise count and the associated calorie burn.

What is claimed is:

1. A treadmill, comprising:
   a frame;
   an exercise deck attached to the frame;
   a console supported by the frame; and
   a body-weight handle connected to the frame;
   a sensor configured to measure at least one parameter of an exercise performed using the body-weight handle; and
   a processor and memory, the memory including programmed instructions which, when accessed by the processor, cause the processor to:
   determine a calorie count per exercise based on the at least one parameter of the exercise;
   determine a number of repetitions of the exercise; and
   based on the number of repetitions and the at least one parameter, determine a body weight calorie burn.

2. The treadmill of claim 1, wherein the sensor is a first sensor, the exercise is a first exercise, and the body-weight handle is a first body-weight handle, and further comprising a second sensor configured to measure a second parameter of a second exercise performed using a second body-weight handle, wherein the programmed instructions further cause the processor to determine whether a user is performing the first exercise or the second exercise.

3. The treadmill of claim 2, wherein the calorie count per exercise is a first calorie count per exercise, the number of repetitions is a first number of repetitions, and the body weight calorie burn is a first body weight calorie burn, and wherein the programmed instructions further cause the processor to:
   determine a second calorie count per exercise based on the second parameter of the second exercise;
   determine a second number of repetitions of the second exercise; and
   based on the second number of repetitions and the second parameter of the second exercise, determine a second body weight calorie burn.

4. The treadmill of claim 3, wherein the programmed instructions further cause the processor to:
   determine an exercise deck calorie burn; and
   determine a workout calorie burn based on the exercise deck calorie burn, the first body weight calorie burn, and the second body weight calorie burn.

5. The treadmill of claim 1, wherein the programmed instructions further cause the processor to determine an exercise deck calorie burn.

6. The treadmill of claim 5, wherein the programmed instructions further cause the processor to determine a workout calorie burn value based on the exercise deck calorie burn and the body weight calorie burn.

7. The treadmill of claim 1, wherein the at least one parameter of the exercise includes an angle of a user while performing the exercise.

8. The treadmill of claim 1, wherein the at least one parameter of the exercise includes a speed of a user while performing the exercise.

9. The treadmill of claim 1, wherein the exercise includes a dip.

10. The treadmill of claim 1, wherein the programmed instructions further cause the processor to alter the calorie count per exercise based on a change in the at least one parameter.

11. A method for analyzing exercise, comprising:
   performing an exercise deck exercise on an exercise deck of a treadmill;
   determining an exercise deck calorie burn based on performing the exercise deck exercise;
   performing a body weight exercise using a handle connected to a frame of the treadmill;
   measuring at least one parameter of the body weight exercise with a sensor on the handle;
   determining a calorie count per exercise using the at least one parameter;
   determining a number of repetitions of the body weight exercise performed using the sensor;
   determining a the calorie count based on the number of repetitions and the calorie count per exercise; and
   determining a workout calorie burn based on the exercise deck calorie burn and the body weight calorie burn.

12. The method of claim 11, wherein the sensor is a first sensor, the body weight exercise is a first body weight exercise, and the handle is a first handle, and further comprising:
  measuring a second parameter of a second body weight exercise performed using a second handle; and
  determining whether a user is performing the first body weight exercise or the second body weight exercise.

13. The method of claim 12, wherein the calorie count per exercise is a first calorie count per exercise, the number of repetitions is a first number of repetitions, the body weight calorie burn is a first body weight calorie burn, and further comprising:
  determining a second calorie count per exercise based on the second parameter of the second body weight exercise;
  determining a second number of repetitions of the second body weight exercise; and
  based on the second number of repetitions and the second parameter of the second body weight exercise, determining a second body weight calorie burn.

14. The method of claim 13, wherein determining the workout calorie burn includes determining the workout calorie burn based on the exercise deck calorie burn, the first body weight calorie burn, and the second body weight calorie burn.

15. The method of claim 11, wherein measuring the at least one parameter of the body weight exercise includes measuring an angle of a user while performing the exercise.

16. The method of claim 11, wherein measuring the at least one parameter of the body weight exercise includes measuring a speed of a user while performing the exercise.

17. The method of claim 11, further comprising altering the body weight calorie count per exercise based on a change in the at least one parameter.

18. A system for tracking exercise, comprising:
  a frame;
  an exercise deck attached to the frame;
  a console supported by the frame; and
  a first handle connected to the frame;
  a second handle connected to the frame;
  a first sensor configured to measure a first parameter of a first body weight exercise performed using the first handle;
  a second sensor configured to measure a second parameter of a second body weight exercise performed using the second handle; and
  a processor and memory, the memory including programmed instructions which, when accessed by the processor, cause the processor to:
    determine a first calorie count per exercise based on the first parameter;
    determine a second calorie count per exercise based on the second parameter;
    determine a first number of repetitions of the first exercise;
    determine a second number of repetitions of the second exercise;
    based on the first number of repetitions and the first parameter, determine a first body weight calorie burn;
    based on the second number of repetitions and the second parameter, determine a second body weight calorie burn;
    determine an exercise deck calorie burn; and
    display the first body weight calorie burn, the second body weight calorie burn, and the exercise deck calorie burn on the console.

19. The system of claim 18, wherein the programmed instructions further cause the processor to determine a workout exercise calorie burn based on the first body weight calorie burn, the second body weight calorie burn, and the exercise deck calorie burn.

20. The system of claim 18, wherein the first body weight exercise is a dip and the second body weight exercise is a push-up.

* * * * *